United States Patent
Takahashi

(10) Patent No.: US 12,032,153 B2
(45) Date of Patent: Jul. 9, 2024

(54) ENDOSCOPE OBJECTIVE OPTICAL SYSTEM AND ENDOSCOPE

(71) Applicant: OLYMPUS CORPORATION, Hachioji (JP)

(72) Inventor: Yoshihiro Takahashi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 475 days.

(21) Appl. No.: 17/495,834

(22) Filed: Oct. 7, 2021

(65) Prior Publication Data
US 2022/0026702 A1 Jan. 27, 2022

Related U.S. Application Data

(63) Continuation of application No. PCT/JP2019/015648, filed on Apr. 10, 2019.

(51) Int. Cl.
G02B 23/24 (2006.01)
G02B 9/08 (2006.01)

(52) U.S. Cl.
CPC ............. G02B 23/243 (2013.01); G02B 9/08 (2013.01)

(58) Field of Classification Search
CPC ........ G02B 23/243; G02B 9/08; G02B 5/208; G02B 9/60; A61B 1/00
See application file for complete search history.

(56) References Cited

U.S. PATENT DOCUMENTS

| 4,806,001 | A | 2/1989 | Okabe et al. |
| 6,191,896 | B1 | 2/2001 | Itoh |
| 6,233,099 | B1 | 5/2001 | Itoh |
| 7,885,017 | B2 | 2/2011 | Inoue |
| 7,978,423 | B2 | 7/2011 | Takato |

(Continued)

FOREIGN PATENT DOCUMENTS

| JP | S62173415 A | 7/1987 |
| JP | H05150172 A | 6/1993 |

(Continued)

OTHER PUBLICATIONS

Japanese Office Action (and English language translation thereof) dated Mar. 23, 2022, issued in counterpart Japanese Application No. 2021-513093.

(Continued)

*Primary Examiner* — George G. King
*Assistant Examiner* — Anna Smith
(74) *Attorney, Agent, or Firm* — Holtz, Holtz & Volek PC

(57) ABSTRACT

An endoscope objective optical system includes in order from an object side, a front group having a positive refractive power, an aperture stop, and a rear group having a positive refractive power. The front group includes a negative lens which nearest to object, a rear group includes a positive lens which is nearest to image, and the endoscope objective optical system satisfies following conditional expressions (1'''), (2) and (3''').

$$-15.0 < ff/f1 < -4.2 \quad (1''')$$
$$-1.70 < f1/f < -0.95 \quad (2)$$
$$0.6 < g1/g2 < 1.20 \quad (3''')$$

where,
ff denotes a focal length of the positive lens,
f1 denotes a focal length of the negative lens,
f denotes a focal length of the overall endoscope objective optical system,
g1 denotes a focal length of the front group, and
g2 denotes a focal length of the rear group.

6 Claims, 7 Drawing Sheets

(56) References Cited

U.S. PATENT DOCUMENTS

| | | |
|---|---|---|
| 8,107,175 B2 | 1/2012 | Kurashige |
| 8,824,067 B2 | 9/2014 | Takato |
| 9,019,621 B2 | 4/2015 | Takada et al. |
| 9,939,627 B2 | 4/2018 | Eguchi |
| 10,101,575 B2 | 10/2018 | Katakura |
| 10,649,201 B2 | 5/2020 | Takato |
| 10,670,854 B2 | 6/2020 | Katakura |
| 10,809,521 B2 | 10/2020 | Tsuji |
| 2009/0052059 A1* | 2/2009 | Lin .................. G02B 23/243 359/755 |
| 2009/0237811 A1 | 9/2009 | Inoue |
| 2010/0046093 A1 | 2/2010 | Takato |
| 2011/0080659 A1 | 4/2011 | Kurashige |
| 2013/0163094 A1 | 6/2013 | Takada et al. |
| 2013/0314805 A1 | 11/2013 | Takato |
| 2016/0154230 A1 | 6/2016 | Katakura |
| 2016/0202452 A1* | 7/2016 | Kuo .................. G02B 27/0025 359/708 |
| 2017/0242237 A1* | 8/2017 | Eguchi .............. G02B 23/243 |
| 2018/0003944 A1* | 1/2018 | Fujii .................. G02B 23/2438 |
| 2018/0314054 A1 | 11/2018 | Takato |
| 2018/0373018 A1 | 12/2018 | Katakura |
| 2019/0064500 A1 | 2/2019 | Tsuji |

FOREIGN PATENT DOCUMENTS

| | | |
|---|---|---|
| JP | H1010425 A | 1/1998 |
| JP | H1184243 A | 3/1999 |
| JP | 2006051132 A | 2/2006 |
| JP | 2008224842 A | 9/2008 |
| JP | 2009258659 A | 11/2009 |
| JP | 2011076021 A | 4/2011 |
| JP | 2012113016 A | 6/2012 |
| JP | 2012252253 A | 12/2012 |
| JP | 2013109179 A | 6/2013 |
| JP | 2013160901 A | 8/2013 |
| JP | 2015018086 A | 1/2015 |
| JP | 2016065954 A | 4/2016 |
| JP | 2016126275 A | 7/2016 |
| JP | 2019032407 A | 2/2019 |
| WO | 2013077139 A1 | 5/2013 |
| WO | 2015025843 A1 | 2/2015 |
| WO | 2016208367 A1 | 12/2016 |
| WO | 2017119188 A1 | 7/2017 |
| WO | 2018042797 A1 | 3/2018 |

OTHER PUBLICATIONS

International Preliminary Report on Patentability (IPRP) (and English language translation thereof) dated Oct. 21, 2021, issued in counterpart International Application No. PCT/JP2019/015648.

International Search Report (ISR) (and English translation thereof) dated Jul. 9, 2019 issued in International Application No. PCT/JP2019/015648.

Written Opinion dated Jul. 9, 2019 issued in International Application No. PCT/JP2019/015648.

* cited by examiner

ENDOSCOPE OBJECTIVE OPTICAL SYSTEM AND ENDOSCOPE

CROSS-REFERENCE TO RELATED APPLICATION

The present application is a continuation application of PCT/JP2019/015648 filed on Apr. 10, 2019; the entire contents of which are incorporated herein by reference.

BACKGROUND

Technical Field

The disclosure relates to an objective optical system. The disclosure relates to an endoscope objective optical system which is used particularly in a medical field and an industrial field.

Description of the Related Art

An endoscope is an apparatus which is widely used in a medical field and an industrial field. Particularly, in the medical field, images of various parts inside a body cavity are achieved by an endoscope inserted into the body cavity. A diagnosis of parts observed, such as screening and close examination, and a procedure such as a treatment, are carried out by using the images acquired.

In an endoscope objective optical system, by adjusting an F-number and a focusing position appropriately, a depth of field suitable for observation inside the body cavity is secured. Moreover, it is desirable that an endoscope secures a minimal invasiveness of a patient, improves an accuracy of diagnosis, and improves a treatability. From this viewpoint, achieving a high quality of an image observed has been sought while reducing a size of an insertion portion of an endoscope front end.

Endoscope objective optical systems having a small size have been proposed in Japanese Patent Application Laid-open Publication No. Hei 10-010425, Japanese Patent Application Laid-open Publication No. 2009-258659, Japanese Patent Application Laid-open Publication No. Hei 5-150172, Japanese Patent Application Laid-open Publication No. 2006-51132, International Unexamined Patent Application Publication No. 2016/208367, International Unexamined Patent Application Publication No. 2013-077139, and International Unexamined Patent Application Publication No. 2018-042797.

SUMMARY

An endoscope objective optical system according to at least some embodiments of the disclosure includes in order from an object side, a front group having a positive refractive power, an aperture stop, and a rear group having a positive refractive power, wherein the front group includes a negative lens which is nearest to object, the rear group includes a positive lens which is nearest to image, the negative lens has a planoconcave shape with a flat surface directed toward the object side, and the endoscope objective optical system satisfies following conditional expressions (1'''), (2), and (3''').

$$-15.0 < ff/f1 < -4.2 \quad (1''')$$

$$-1.70 < f1/f < -0.95 \quad (2)$$

$$0.6 < g1/g2 < 1.20 \quad (3''')$$

where, ff denotes a focal length of the positive lens, f1 denotes a focal length of the negative lens, f denotes a focal length of the overall endoscope objective optical system, g1 denotes a focal length of the front group, and g2 denotes a focal length of the rear group.

Moreover, an endoscope according to at least some embodiments of the disclosure includes the abovementioned endoscope objective optical system.

DETAILED DESCRIPTION

Prior to description of examples, advantageous effects of an embodiment according to a certain aspect of the disclosure will be described below. While describing specifically the advantageous effects of the present embodiment, the description will be made by citing specific examples. However, similarly as a case of examples to be described later, aspects illustrated are some of the aspects included in the disclosure, and there exists a large number of variations for these aspects. Therefore, the disclosure is not restricted to the aspect to be illustrated.

Figure 1:
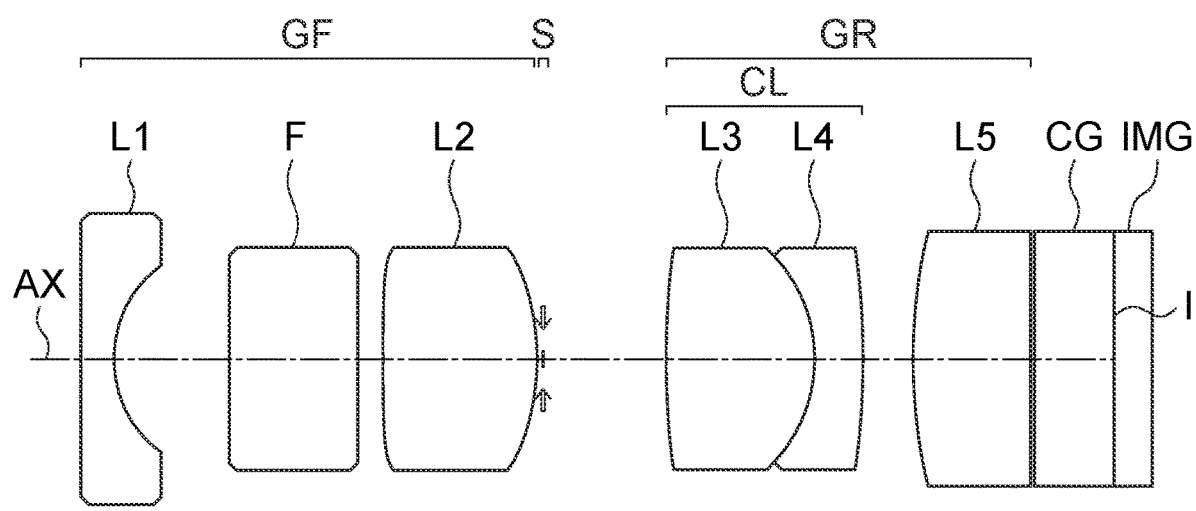
FIG. 1 is a diagram showing a cross-sectional view of an overall lens arrangement of an endoscope objective optical system according to an embodiment of the disclosure.

FIG. 1 is a diagram showing a cross-sectional view of a lens arrangement of an endoscope objective optical system according to an embodiment of the disclosure.

Generally, it is necessary to observe a wide range of area by an endoscope. At the same time, an outer diameter of a lens nearest to an object has to be made small. Therefore, in the present disclosure, a retro focus arrangement is adopted.

The endoscope objective optical system according to the embodiment of the disclosure consists of in order from an object side, a front group GF having a positive refractive power, an aperture stop S, and a rear group GR having a positive refractive power, wherein the front group GF includes a negative lens L1 which is nearest to the object, and the rear group GR includes a positive lens L5 which is nearest to an image, and following conditional expressions (1) and (2) are satisfied.

$$-15.0 < ff/f1 < -3.8 \quad (1)$$

$$-1.70 < f1/f < -0.95 \quad (2)$$

where, ff denotes a focal length of the positive lens L5, f1 denotes a focal length of the negative lens L1, and f denotes a focal length of the overall endoscope objective optical system.

The negative lens L1 is disposed nearest to the object in the front group GF and a negative refractive power necessary for a retro focus arrangement is secured. Moreover, when an aberration correction is taken into consideration, it is desirable that an arrangement of refractive power before and after the aperture stop S is symmetric. Therefore, in the present embodiment, both the front group GF and the rear group GR are arranged to have a positive refractive power.

Moreover, for achieving a high-quality image, when a pixel pitch of an image sensor IMG is made small, a permissible circle of confusion becomes small. Therefore, for securing a depth of field appropriate for observation, it is necessary to carry out a focusing position adjustment with high accuracy.

Moreover, in a wide-angle endoscope objective optical system having a small-size image sensor IMG installed therein, for suppressing an asymmetry of an angle of view, an alignment of an optical axis and a center of the image sensor IMG has to be carried out with high accuracy. Furthermore, even when these adjustments are carried out with high accuracy, the asymmetry of the angle of view and a variation in the focusing position due to cure shrinkage of an adhesive occur.

Therefore, in the present embodiment, the lens L5 having a positive refractive power is disposed nearest to the image in the rear group GR. Accordingly, an optical magnification is made small when the positive lens L5 and the image sensor IMG have moved together. Thus, an arrangement is made so as to enable reduction of the variation in the focusing position and a manufacturing error sensitivity of the asymmetry of the angle of view. The positive lens L5 has a function of a field lens.

At this time, taking into consideration the variation in the focusing position and the manufacturing error sensitivity of the asymmetry of the angle of view, it is necessary that the positive lens L5 in the rear group GR corrects various aberrations, particularly, a curvature of field, that occur in the negative lens L1.

Furthermore, the negative lens L1 which forms the negative refractive power of the retro focus has an effect on an error sensitivity of the angle of view. Therefore, it is desirable that the endoscope objective optical system satisfies following conditional expression (1).

$$-15.0 < ff/f1 < -3.8 \quad (1)$$

where, ff denotes a focal length of the positive lens L5, and f1 denotes a focal length of the negative lens L1.

Conditional expression (1) is related to a ratio of the focal length of the negative lens L1 and the focal length of the positive lens L5. When an upper limit value of conditional expression (1) is exceeded, an amount of aberration which occurs in the positive lens L5 becomes large, the curvature of field is deteriorated.

When a value falls below a lower limit value of conditional expression (1), the refractive power of the positive lens L5 becomes small, and the variation in the focusing position and the manufacturing error sensitivity of asymmetry of the angle of view become high. Furthermore, an amount of an aberration which occurs at the negative lens L1 becomes large, and either the curvature of field is deteriorated or the manufacturing error sensitivity related to the angle of view becomes high.

Moreover, for making small an outer diameter of the negative lens L1 and shortening the overall length of the optical system while reducing the curvature of field and the manufacturing error sensitivity of the angle of view, it is necessary to have the refractive power of the negative lens L1 set appropriately. For this, it is desirable to satisfy following conditional expression (2).

$$-1.70 < f1/f < -0.95 \quad (2)$$

where, f1 denotes a focal length of the negative lens L1, and f denotes a focal length of the overall endoscope objective optical system.

Conditional expression (2) is related to a ratio of the focal length of the overall endoscope objective optical system and the focal length of the negative lens L1. When an upper limit value of conditional expression (2) is exceeded, an amount of aberration which occurs at the negative lens L1 becomes large, and the curvature of field and a coma are deteriorated.

When a value falls below a lower limit value of conditional expression (2), the refractive power of the negative lens L1 becomes small, and because a light-ray Neigh at the negative lens L1 becomes high, it becomes difficult to make the outer diameter of the negative lens L1 small and to shorten the overall length of the optical system.

It is more desirable to satisfy following conditional expression (1') instead of conditional expression (1).

$$-10.0 < ff/f1 < -4.2 \quad (1')$$

Moreover, it is even more desirable to satisfy following conditional expression (1") instead of conditional expression (1).

$$-8.0 < ff/f1 < -4.7 \quad (1")$$

It is more desirable to satisfy following conditional expression (2') instead of conditional expression (2).

$$-1.6 < f1/f < -1.0 \quad (2')$$

Moreover, it is even more desirable to satisfy following conditional expression (2″) instead of conditional expression (2).

$$-1.5 < f1/f < -1.1 \quad (2'')$$

Moreover, according to a preferable aspect of the present embodiment, it is desirable to satisfy following conditional expression (3).

$$0.35 < g1/g2 < 1.20 \quad (3)$$

where,
g1 denotes a focal length of the front group GF, and
g2 denotes a focal length of the rear group GR.

Conditional expression (3) is related to a ratio of the focal length of the front group GF and the focal length of the rear group GR. In an endoscope objective optical system using a retro focus arrangement, a lens having a large negative refractive power is disposed in the front group GF. When an aberration correction of the overall optical system is taken into consideration, it is necessary to control a refractive power arrangement before and after the aperture stop S.

When an upper limit value of conditional expression (3) is exceeded, an image plane is inclined toward an over-side, and the astigmatism is deteriorated.

When a value falls below a lower limit value of conditional expression (3), a symmetry before and after the aperture stop S is broken, and it is not possible to correct adequately the chromatic aberration of magnification and the curvature of field.

It is more desirable to satisfy following conditional expression (3′) instead of conditional expression (3).

$$0.5 < g1/g2 < 1.0 \quad (3')$$

Moreover, it is even more desirable to satisfy following conditional expression (3″) instead of conditional expression (3).

$$0.6 < g1/g2 < 0.8 \quad (3'')$$

Moreover, according to a preferable aspect of the present embodiment, it is desirable to satisfy following conditional expression (4).

$$1.2 < g1/f < 0.5 \quad (4)$$

where,
g1 denotes the focal length of the front group GF, and
f denotes the focal length of the overall endoscope objective optical system.

Conditional expression (4) is related to a ratio of the focal length of the overall optical system and the focal length of the front group GF. In the present embodiment, the negative refractive power of the retro focus is formed in the front group GF. Moreover, an arrangement is made such that both the front group GF and the rear group GR with the aperture stop S in between, have a positive refractive power. Therefore, the front group GF is to include the negative lens L1 and at least one or more than one positive lenses. For reducing the sensitivity of manufacturing error of a lens and making small the outer diameter of a lens in the front group GF, it is necessary to set appropriately the refractive power of the front group GF.

When an upper limit value of conditional expression (4) is exceeded, the refractive power of the front group GF becomes small, and the overall length of the optical system becomes large. Moreover, it becomes difficult to make the lens in the front group small.

When a value falls below a lower limit value of conditional expression (4), the manufacturing error sensitivity of the lens in the front group GF becomes high, and when the lens has moved in an optical axial direction or a direction perpendicular to an optical axis AX, it becomes difficult to suppress the variation in the angle of view and the curvature of field.

It is more desirable to satisfy following conditional expression (4′) instead of conditional expression (4).

$$1.5 < g1/f < 4.0 \quad (4')$$

Moreover, it is even more desirable to satisfy following conditional expression (4″) instead of conditional expression (4).

$$1.8 < g1/f < 3.0 \quad (4'')$$

According to a preferable aspect of the present embodiment, it is desirable that the focal length of the rear group GR satisfies following conditional expression (5).

$$2.5 < g2/f < 6.0 \quad (5)$$

where,
g2 denotes the focal length of the rear group GR, and
f denotes the focal length of the overall endoscope objective optical system.

Generally, when the retro focus arrangement is adopted in an optical system, a back focus tends to be long, and the overall length of the optical system tends to become large. Therefore, it is necessary to set appropriately the refractive power of the rear group GR.

Conditional expression (5) is related to a ratio of the focal length of the overall endoscope objective optical system and the focal length of the rear group GR. When an upper limit value of conditional expression (5) is exceeded, the back focus becomes long, and it becomes difficult to shorten the overall length of the optical system.

When a value falls below a lower limit value of conditional expression (5), the back focus becomes excessively short, and it is not possible to secure adequately an amount of adjustment at the time of adjusting the focusing position.

It is more desirable to satisfy following conditional expression (5′) instead of conditional expression (5).

$$2.8 < g2/f < 5.0 \quad (5')$$

Moreover, it is even more preferable to satisfy following conditional expression (5″) instead of conditional expression (5).

$$3.0 < g2/f < 4.0 \quad (5'')$$

According to a preferable aspect of the present embodiment, it is desirable that the focal length of the positive lens L5 satisfies following conditional expression (6).

$$4.0 < ff/f < 20.0 \quad (6)$$

where,
ff denotes the focal length of the positive lens L5, and
f denotes the focal length of the overall endoscope objective optical system.

Conditional expression (6) is related to a ratio of the focal length of the overall endoscope objective optical system and the focal length of the positive lens L5. The refractive power of the positive lens L5 in the rear group GR has an effect on an amount of adjustment necessary for the optical adjustment of the asymmetry of the angle of view, and the focusing position. According to the present embodiment, it is possible to carry out the optical adjustment, for instance, by moving a lens frame including the positive lens L5 and the image sensor IMG in the direction of the optical axis AX or the direction perpendicular to the optical axis AX. Moreover, when the amount of adjustment of asymmetry of the angle of view and the focusing position becomes large, it is necessary to secure adequately a clearance between lens frames to be adhesive-fixed. Consequently, a displacement at the time of cure shrinkage of the adhesive as much as the clearance is susceptible to occur.

When an upper limit value of conditional expression (6) is exceeded, the variation in the focusing position and the manufacturing error sensitivity of the asymmetry of the angle of view become high, and it becomes difficult to suppress degradation of an optical performance.

When a value falls below a lower limit value of conditional expression (6), the variation in the focusing position and the amount of adjustment of the asymmetry of the angle of view become excessively large. Moreover, an amount of aberration which occurs at the positive lens L5 becomes large, and the curvature of field is deteriorated.

It is more desirable to satisfy following conditional expression (6') instead of conditional expression (6).

$$4.5 < ff/f < 15.0 \tag{6'}$$

Moreover, it is even more desirable to satisfy following conditional expression (6") instead of conditional expression (6).

$$5.0 < ff/f < 10.0 \tag{6"}$$

According to a preferable aspect of the present embodiment, it is desirable that the positive lens L5 is either cemented to a cover glass CG or is disposed at a fixed distance from the cover glass CG.

Accordingly, the optical magnification when the positive lens L5 and the image sensor IMG are moved together, is made small. In such manner, an arrangement is made so as to reduce the variation in the focusing position and the manufacturing error sensitivity of the asymmetry of the angle of view. The positive lens L5 has a function of a field lens.

Moreover, according to a preferable aspect of the present embodiment, it is desirable to carry out the focusing position adjustment by changing a distance between the aperture stop S and the positive lens L5.

At the time of assembling an optical system, there is a variation in the focusing position due to a manufacturing error which arises in a range of a component tolerance of a lens and a lens frame. Therefore, the focusing position adjustment is carried out by moving the lens. In the present embodiment, it is desirable to carry out the focusing position adjustment by changing the distance between the aperture stop S and the positive lens L5. Accordingly, an amount of change in the focusing position with respect to the amount of movement decreases, and it becomes easy to adjust the focusing position at the time of assembling. Moreover, it is possible to suppress an amount of degradation of the optical performance due to cure shrinkage of an adhesive.

Furthermore, the asymmetry of the angle of view may be adjusted by moving the positive lens L5 in a direction perpendicular to the optical axis AX. The adjustment of the asymmetry of the angle of view is also possible by selecting an image upon changing arbitrarily an area of use of the image sensor IMG. An arrangement may be made to carry out the adjustment by combining the two.

Moreover, it is desirable to make following arrangement regarding the negative lens L1. In an endoscope, in a case of dirt, blood etc. getting adhered to a lens surface thereby hindering the observation, cleaning of the lens surface is carried out by injecting water from a nozzle provided to an endoscope front end. At this time, in a case in which the lens surface is convex-shaped, the dirt is hard to be removed, and in a case in which the lens surface is concave-shaped, water is accumulated on the lens surface. Particularly, in a case of the convex-shaped lens surface, a scratch or a crack due to an impact is susceptible to occur. Therefore, it is desirable that the negative lens L1 is planoconvex-shaped with a flat surface directed toward the object side.

Moreover, according to a preferable aspect of the present embodiment, an arrangement having a cemented lens CL of a positive lens L3 and a negative lens L4 is desirable. By disposing the cemented lens CL, correction of a longitudinal chromatic aberration and the chromatic aberration of magnification becomes even easier.

Moreover, the image sensor IMG is disposed near an image plane of the endoscope objective optical system. A cover glass CG for preventing the image sensor from being scratched etc. is provided to an image pickup surface I of the image sensor IMG. As mentioned above, it is desirable that the positive lens L5 of the rear group GR is either cemented to the cover glass CG of the image sensor IMG or disposed at a fixed distance from the cover glass by providing a spacer etc.

The abovementioned endoscope objective optical system may satisfy the plurality of arrangements simultaneously. Doing so will enable to achieve even more favorable arrangement from a performance point of view or a manufacturing point of view. Moreover, combinations of the preferable arrangements are arbitrary. Regarding conditional expressions, only an upper limit value or a lower limit value of a numerical range of further restricted conditional expression may be restricted.

Each example will be described below.

EXAMPLE 1

Figure 2A:
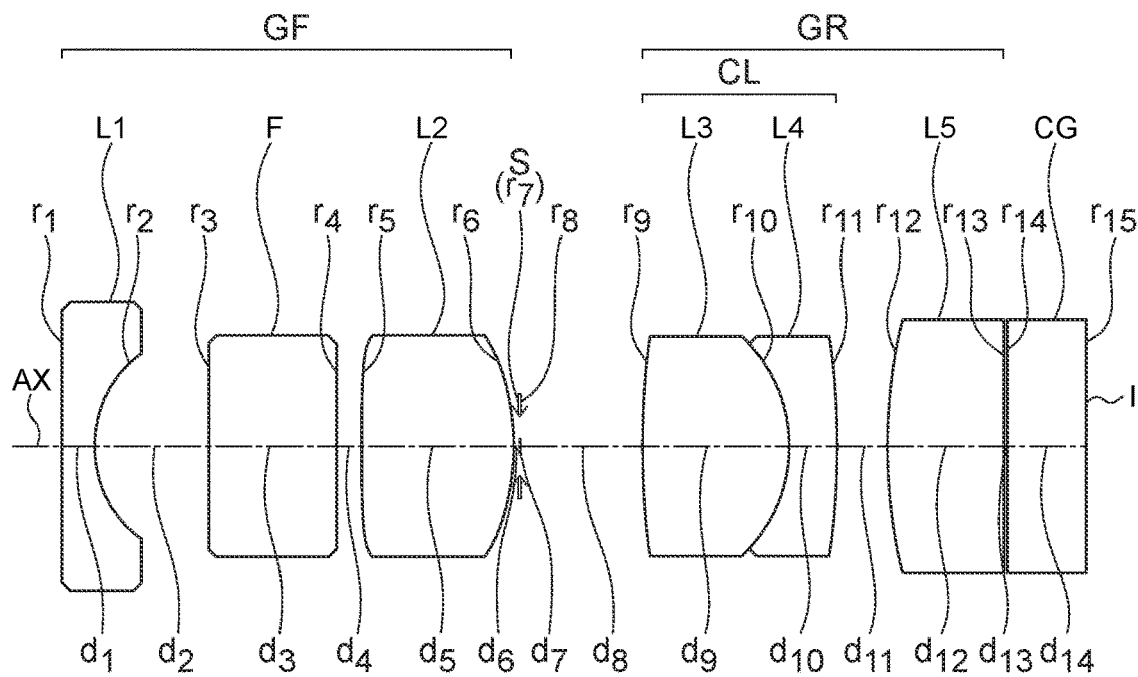
FIG. 2A is a diagram showing a cross-sectional view of a lens arrangement of an endoscope objective optical system according to an example 1 of the disclosure.
Figures 2B, 2C, 2D, 2E:
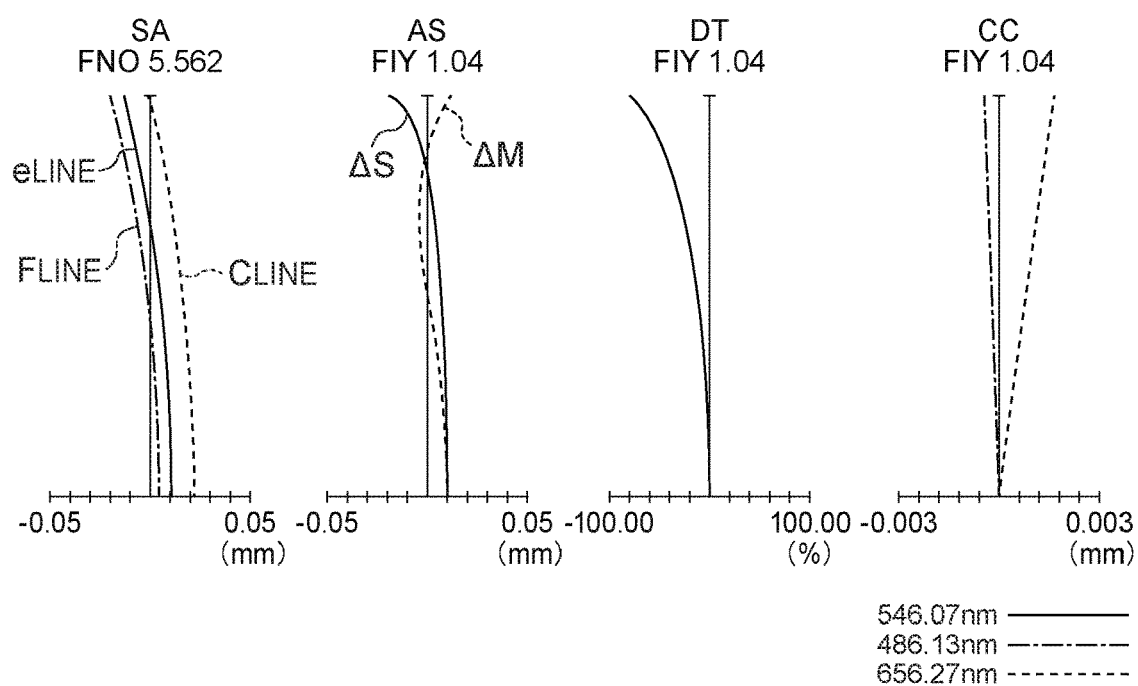
FIG. 2B, FIG. 2C, FIG. 2D, and FIG. 2E are aberration diagrams showing a spherical aberration (SA), an astigmatism (AS), a distortion (DT), and a chromatic aberration of magnification (CC) respectively, of the example 1.

An endoscope objective optical system according to an example 1 will be described below. FIG. 2A is a diagram showing a cross-sectional view of a lens arrangement of the endoscope objective optical system according to the present example.

The endoscope objective optical system according to the present example consists of in order from an object side, a front group GF having a positive refractive power, an aperture stop S, and a rear group GR having a positive refractive power.

The front group GF includes in order from the object side, a first lens L1 which is a planoconcave negative lens having a flat surface directed toward the object side, an infrared absorbing filter F, and a second lens L2 which is a biconvex positive lens. The aperture stop S is disposed between the front group GF and the rear group GR. The rear group GR includes in order from the object side, a third lens L3 which is a biconvex positive lens, a fourth lens L4 which is a negative meniscus lens having a convex surface directed toward an image side, and a fifth lens L5 which is a planoconvex positive lens having a flat surface directed toward the image side. A cover glass CG is disposed on the image side of the rear group GR. The fifth lens L5 is a field lens.

Moreover, a YAG (yttrium aluminum garnet) laser cut coating is applied to an object side of the infrared absorbing filter F, and a semiconductor laser cut coating is applied to an image side of the infrared absorbing filter F.

Here, the third lens L3 having a positive refractive power and the fourth lens L4 which is a negative meniscus lens are cemented, and form a cemented lens CL. Moreover, a flat surface of the fifth lens L5 which is a planoconvex positive lens is cemented to the cover glass CG formed on an image pickup surface I.

FIG. 2B, FIG. 2C, FIG. 2D, and FIG. 2E are aberration diagrams showing a spherical aberration (SA), an astigmatism (AS), a distortion (DT), and a chromatic aberration of magnification (CC) respectively, of the example 1.

The aberration diagrams show aberration for each of wavelengths 656.3 nm (C-line), 486.1 nm (F-line), and 546.1 nm (e-line). Aberration diagrams below show aberration for the same wavelengths.

EXAMPLE 2

Figure 3A:
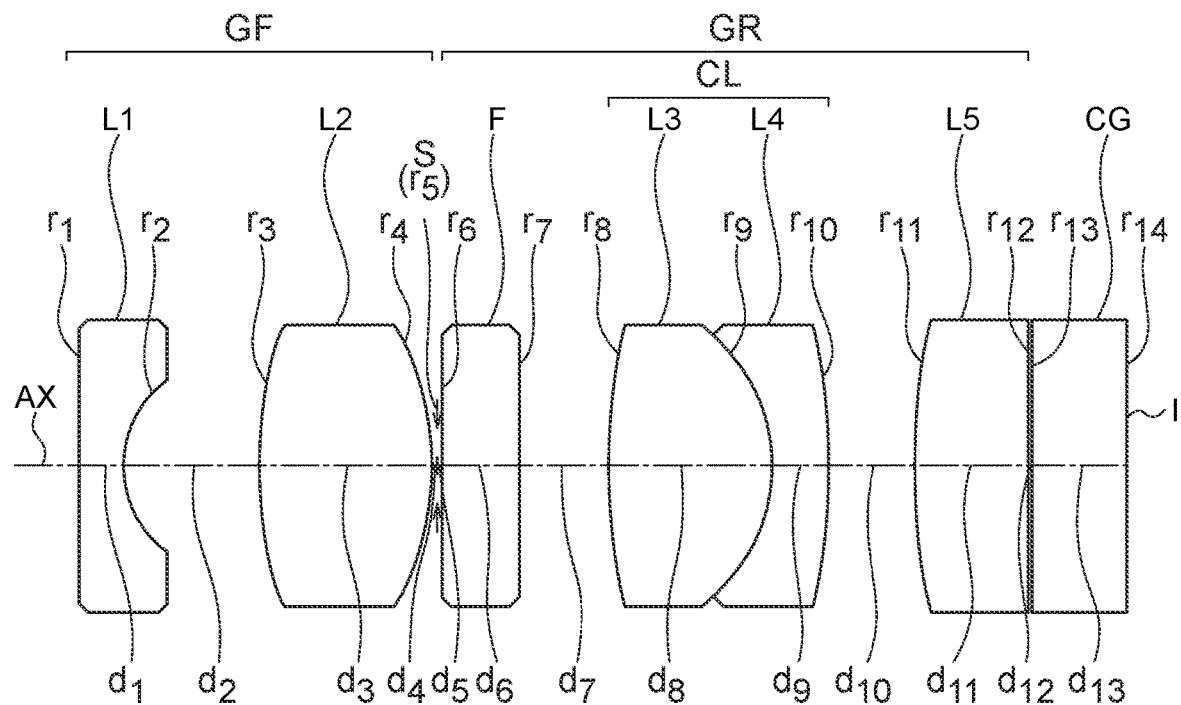
FIG. 3A is a diagram showing a cross-sectional view of a lens arrangement of an endoscope objective optical system according to an example 2 of the disclosure.
Figures 3B, 3C, 3D, 3E:
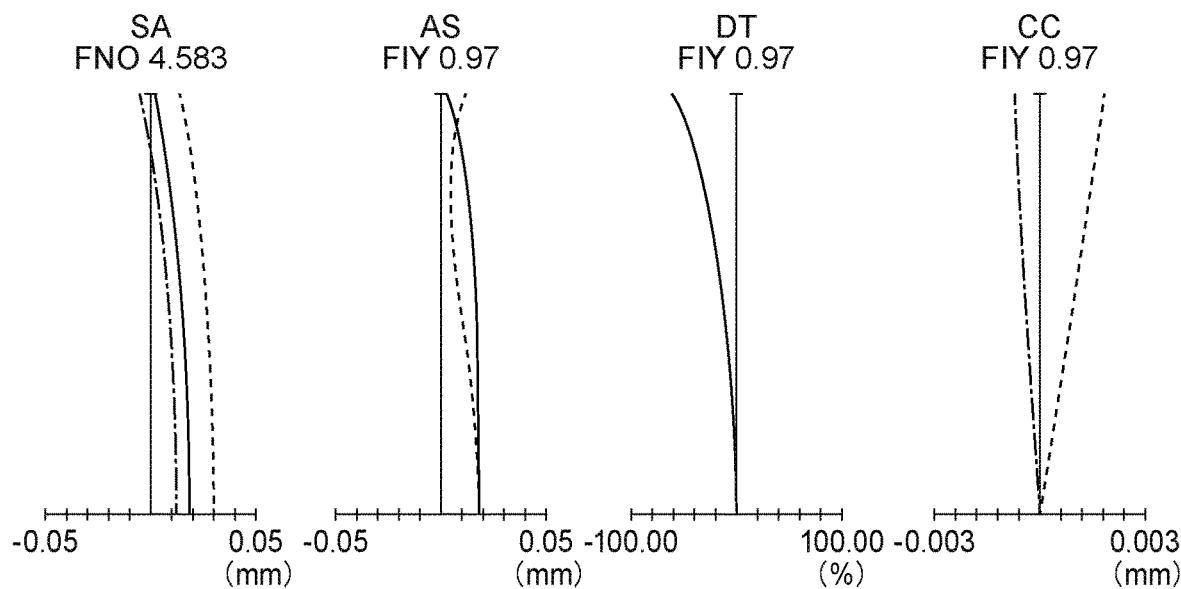
FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively, of the example 2.

An endoscope objective optical system according to an example 2 will be described below. FIG. 3A is a diagram showing a cross-sectional view of a lens arrangement of the endoscope objective optical system according to the present example.

The endoscope objective optical system according to the present example consists of in order from an object side, a front group GF having a positive refractive power, an aperture stop S, and a rear group GR having a positive refractive power.

The front group GF includes in order from the object side, a first lens L1 which is a planoconcave negative lens having a flat surface directed toward the object side and a second lens L2 which is a biconvex positive lens. The aperture stop S is disposed between the front group GF and the rear group GR. The rear group GR includes in order from the object side, an infrared absorbing filter F, a third lens L3 which is a biconvex positive lens, a fourth lens L4 which is a negative meniscus lens having a convex surface directed toward an image side, and a fifth lens L5 which is a planoconvex positive lens having a flat surface directed toward the image side. A cover glass CG is disposed on the image side of the rear group GR. The fifth lens L5 is a field lens.

Moreover, a YAG laser cut coating is applied to an object side of the infrared absorbing filter F, and a semiconductor laser cut coating is applied to an image side of the infrared absorbing filter F.

Here, the third lens L3 having a positive refractive power and the fourth lens L4 which is a negative meniscus lens are cemented, and form a cemented lens CL. Moreover, the flat surface of the fifth lens L5 which is a planoconvex positive lens is cemented to the cover glass CG formed on an image pickup surface I.

FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively, of the example 2.

EXAMPLE 3

Figure 4A:
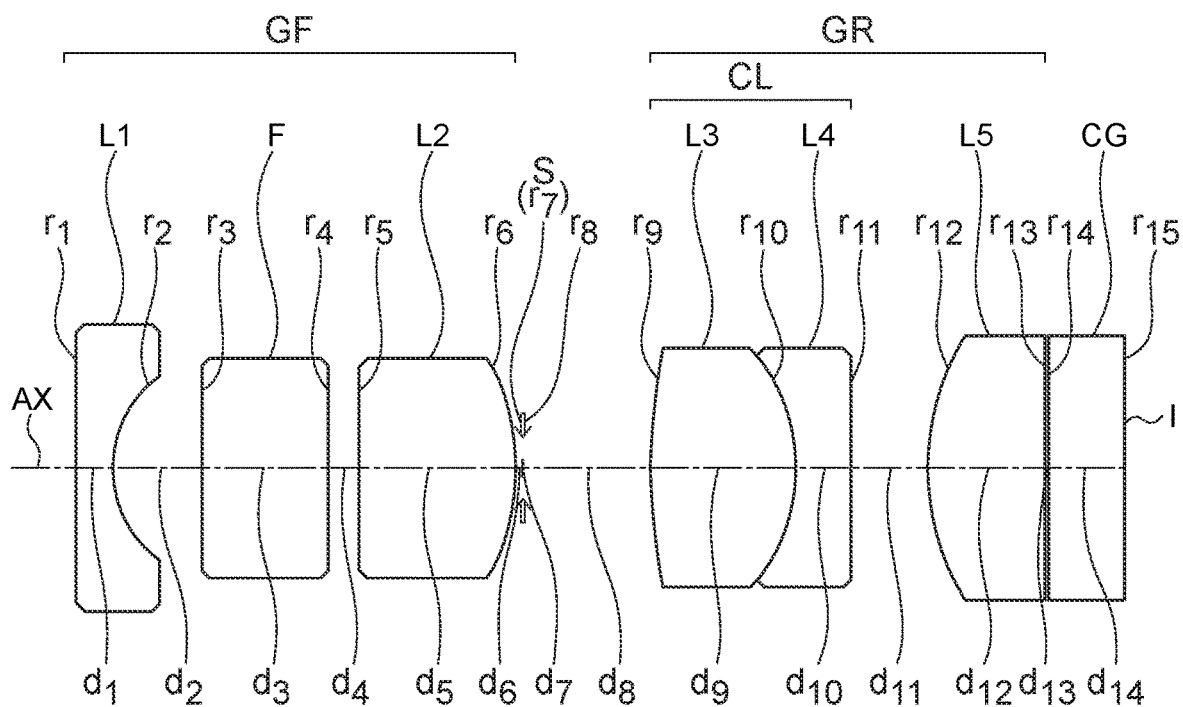
FIG. 4A is a diagram showing a cross-sectional view of a lens arrangement of an endoscope objective optical system according to an example 3 of the disclosure.
Figures 4B, 4C, 4D, 4E:
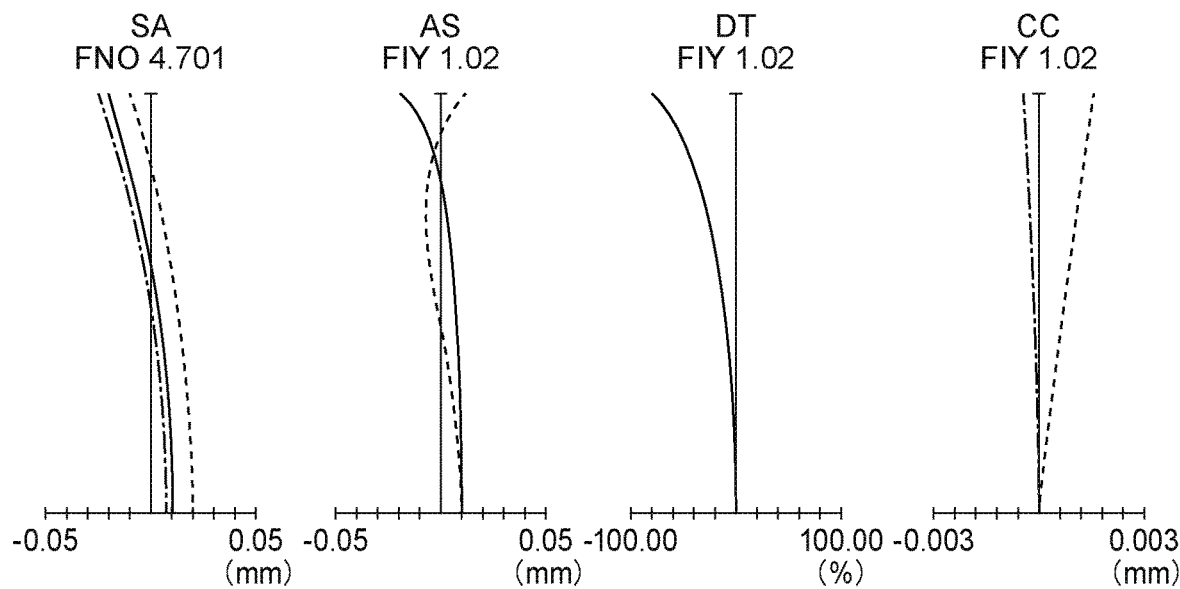
FIG. 4B, FIG. 4C, FIG. 4D, and FIG. 4E are aberration diagrams showing a spherical aberration (SA), and astigmatism (AS), a distortion (DT), and a chromatic aberration of magnification (CC) respectively, of the example 3.

An endoscope objective optical system according to an example 3 will be described below. FIG. 4A is a diagram showing a cross-sectional view of a lens arrangement of the endoscope objective optical system according to the present example.

The endoscope objective optical system according to the present example consists of in order from an object side, a front group GF having a positive refractive power, an aperture stop S, and a rear group GR having a positive refractive power.

The front group GF includes in order from the object side, a first lens L1 which is a planoconcave negative lens having a flat surface directed toward the object side, an infrared absorbing filter F, and a second lens L2 which is a planoconvex positive lens having a flat surface directed toward the object side. The aperture stop S is disposed between the front group GF and the rear group GR. The rear group GR includes in order from the object side, a third lens L3 which is a biconvex positive lens, a fourth lens L4 which is a planoconcave negative lens having a flat surface directed toward an image side, and a fifth lens L5 which is a planoconvex positive lens having a flat surface directed toward the image side. A cover glass CG is disposed on the image side of the rear group GR. The fifth lens L5 is a field lens.

Moreover, a YAG laser cut coating is applied to an object side of the infrared absorbing filter F, and a semiconductor laser cut coating is applied to an image side of the infrared absorbing filter F.

Here, the third lens L3 having a positive refractive power and the fourth lens L4 having a negative refractive power are cemented, and form a cemented lens CL. Moreover, the flat surface of the fifth lens L5 which is a planoconvex positive lens is cemented to the cover glass CG formed on an image pickup surface I.

FIG. 4B, FIG. 4C, FIG. 4D, and FIG. 4E are aberration diagrams showing a spherical aberration (SA), an astigmatism (AS), a distortion (DT), and a chromatic aberration of magnification (CC) respectively, of the example 3.

EXAMPLE 4

Figure 5A:
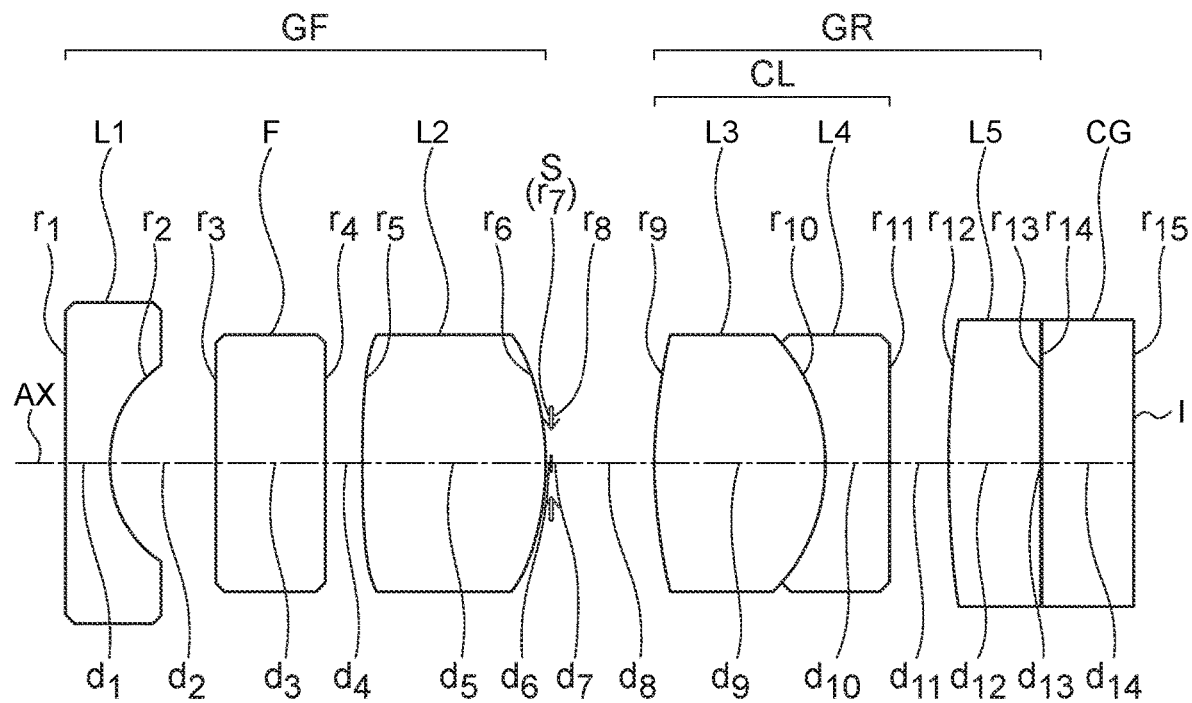
FIG. 5A is a diagram showing a cross-sectional view of a lens arrangement of an endoscope objective optical system according to an example 4 of the disclosure.
Figures 5B, 5C, 5D, 5E:
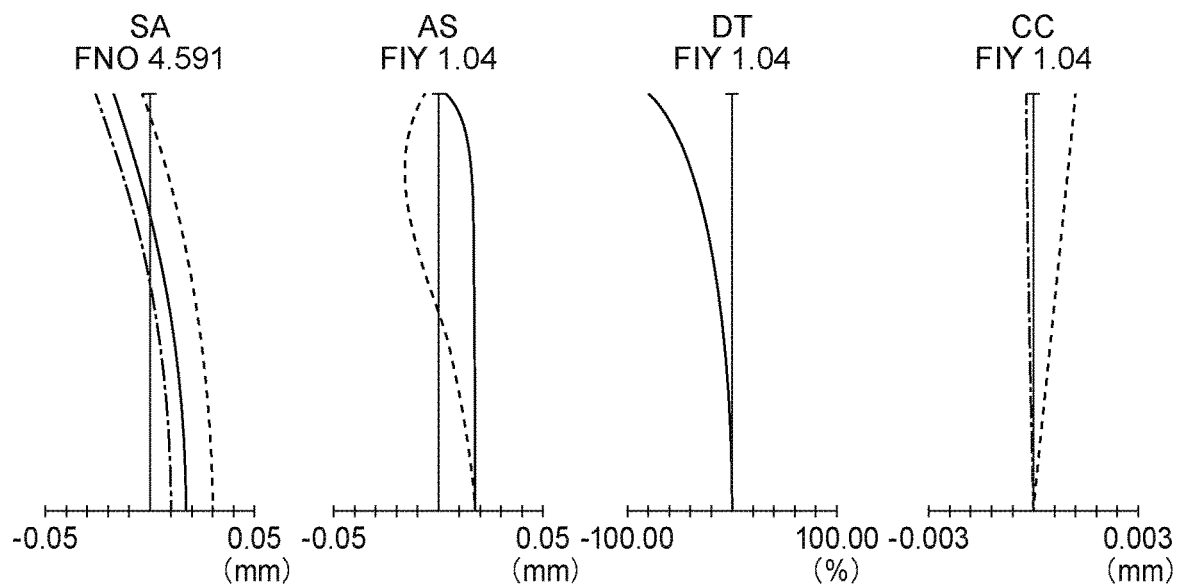
FIG. 5B, FIG. 5C, FIG. 5D, and FIG. 5E are aberration diagrams showing a spherical aberration (SA), an astigmatism (AS), a distortion (DT), and a chromatic aberration of magnification (CC) respectively, of the example 4.

An endoscope objective optical system according to an example 4 will be described below. FIG. 5A is a diagram showing a cross-sectional view of a lens arrangement of the endoscope objective optical system according to the present example.

The endoscope objective optical system according to the present example consists of in order from an object side, a front group GF having a positive refractive power, an aperture stop S, and a rear group GR having a positive refractive power.

The front group GF includes in order from the object side, a first lens which is a planoconcave negative lens having a flat surface directed toward the object side, an infrared absorbing filter F, and a second lens L2 which is a biconvex positive lens. The aperture stop S is disposed between the front group GF and the rear group GR. The rear group GR includes a third lens L3 which is a biconvex positive lens, a fourth lens L4 which is a planoconcave negative lens having a flat surface directed toward an image side, and a fifth lens L5 which is a planoconvex positive lens having a flat surface directed toward the image side. A cover glass CG is disposed on the image side of the rear group GR. The fifth lens L5 is a field lens.

Moreover, a YAG laser cut coating is applied to an object side of the infrared absorbing filter F, and a semiconductor laser cut coating is applied to an image side of the infrared absorbing filter F.

Here, the third lens L3 having a positive refractive power and the fourth lens L4 having a negative refractive power are cemented, and form a cemented lens CL. Moreover, the flat surface of the lens L5 which is a planoconvex positive lens is cemented to a cover glass CG formed on an image pickup surface.

FIG. 5B, FIG. 5C, FIG. 5D, and FIG. 5E are aberration diagrams showing a spherical aberration (SA), an astigmatism (AS), a distortion (DT), and a chromatic aberration of magnification (CC) respectively, of the example 4.

EXAMPLE 5

Figure 6A:
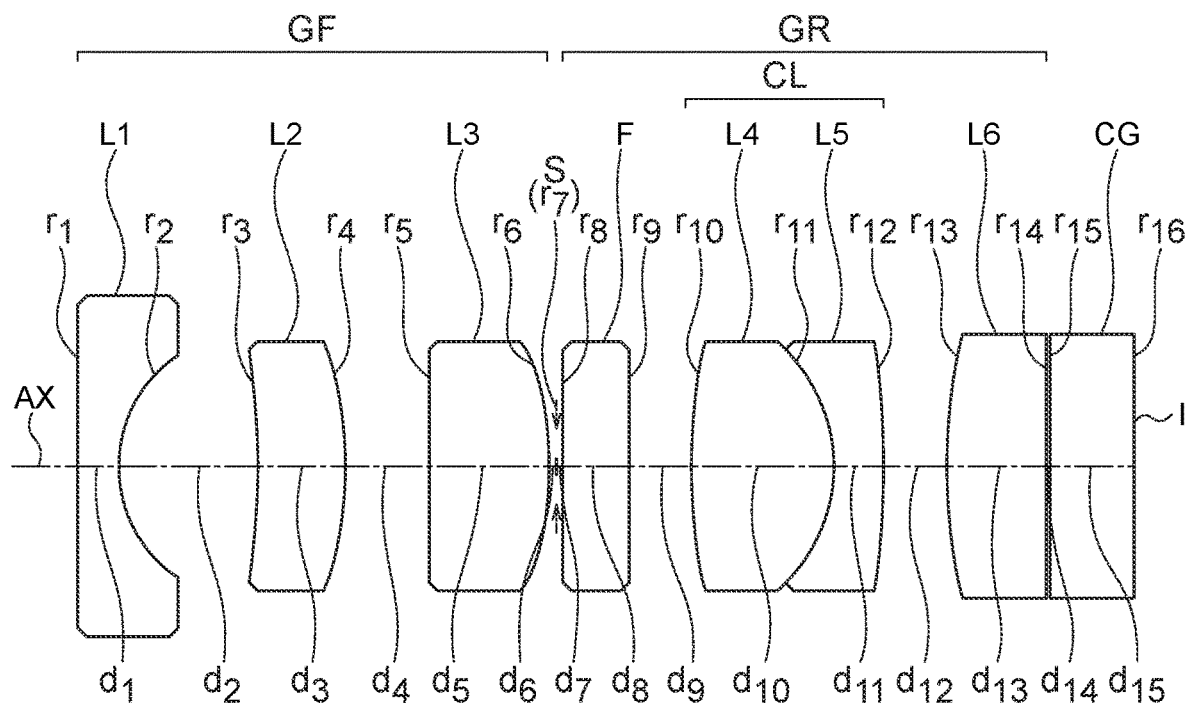
FIG. 6A is a diagram showing a cross-sectional view of a lens arrangement of an endoscope objective optical system according to an example 5 of the disclosure.
Figures 6B, 6C, 6D, 6E:
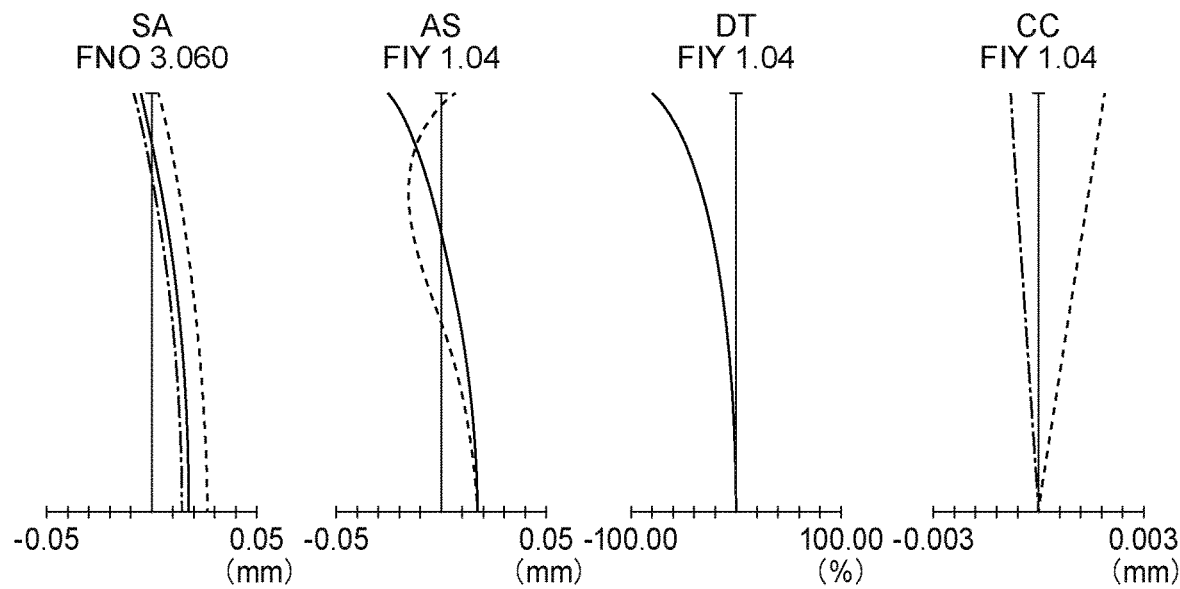
FIG. 6B, FIG. 6C, FIG. 6D, and FIG. 6E are aberration diagrams showing a spherical aberration (SA), an astigmatism (AS), a distortion (DT), and a chromatic aberration of magnification (CC) respectively, of the example 5.

An endoscope objective optical system according to an example 5 will be described below. FIG. 6A is a diagram showing a cross-sectional view of a lens arrangement of the endoscope objective optical system according to the present example.

The endoscope objective optical system according to the present example consists of in order from an object side, a front group GF having a positive refractive power, an aperture stop S, and a rear group GR having a positive refractive power.

The front group GF includes in order from the object side, a first lens L1 which is a planoconcave negative lens having a flat surface directed toward the object side, a second lens L2 which is a positive meniscus lens having a convex surface directed toward an image side, and a third lens L3 which is a planoconvex positive lens having a flat surface directed toward the object side. The aperture stop S is disposed between the front group GF and the rear group GR. The rear group GR includes an infrared absorbing filter F, a fourth lens L4 which is a biconvex positive lens, a fifth lens L5 which is a negative meniscus lens having a convex surface directed toward the image side, and a sixth lens L6 which is a planoconvex positive lens having a flat surface directed toward the image side. A cover glass CG is disposed on the image side of the rear group GR. The sixth lens L6 is a field lens.

Moreover, a YAG laser cut coating is applied to an object side of an infrared absorbing filter F, and a semiconductor laser cut coating is applied to an image side of the infrared absorbing filter F.

Here, the fourth lens L4 having a positive refractive power and a fifth lens L5 having a negative refractive power are cemented, and form a cemented lens CL. Moreover, the sixth lens L6 is disposed leaving a fixed distance by providing a spacer between a cover glass CG formed on an image pickup surface and the sixth lens L6.

FIG. 6B, FIG. 6C, FIG. 6D, and FIG. 6E are aberration diagrams showing a spherical aberration (SA), an astigmatism (AS), a distortion (DT), and a chromatic aberration of magnification (CC) respectively, of the example 5.

EXAMPLE 6

Figure 7A:
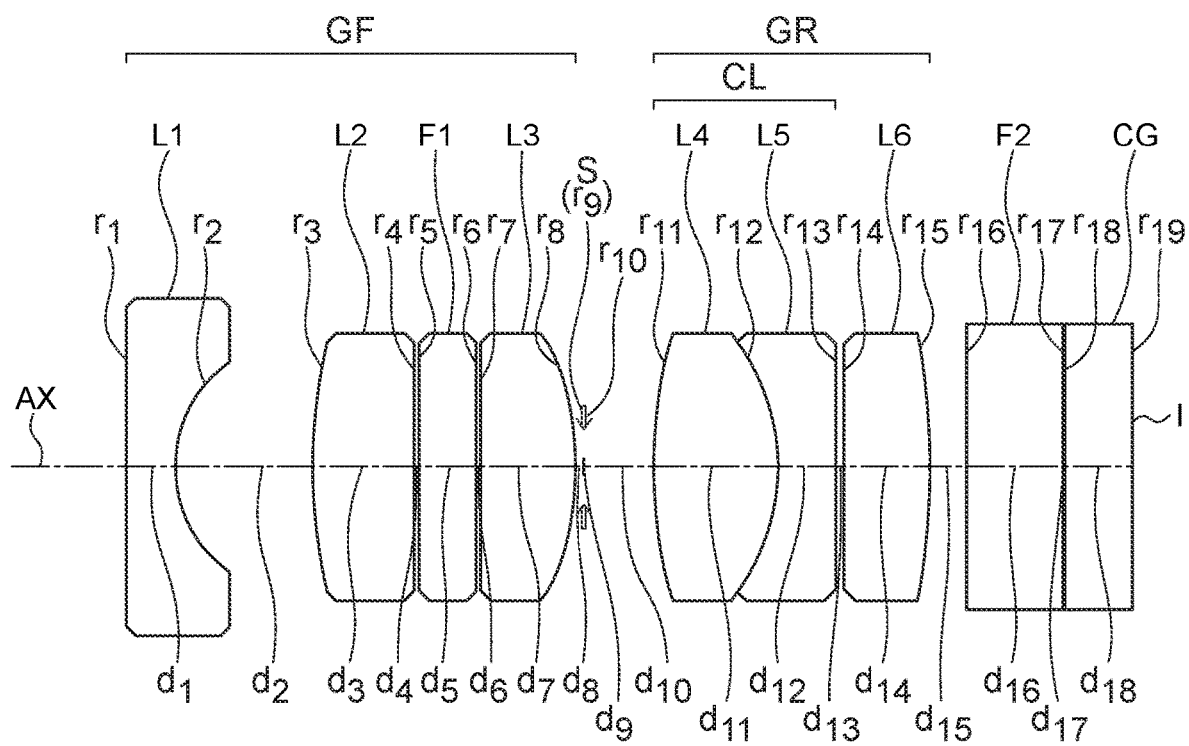
FIG. 7A is a diagram showing a cross-sectional view of a lens arrangement of an endoscope objective optical system according to an example 6 of the disclosure.
Figures 7B, 7C, 7D, 7E:
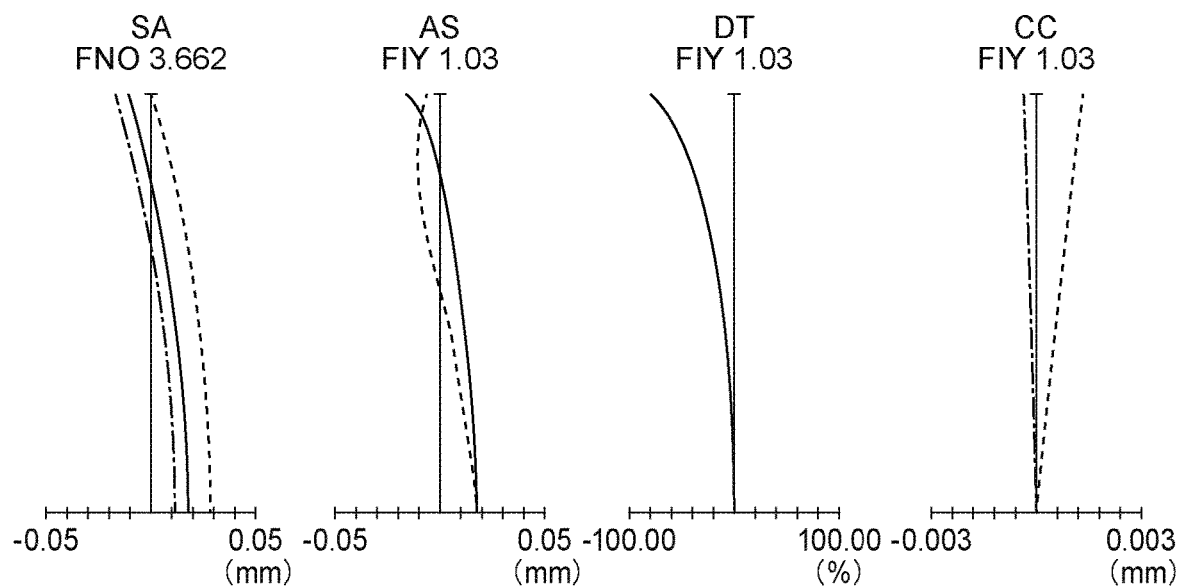
FIG. 7B, FIG. 7C, FIG. 7D, and FIG. 7E are aberration diagrams showing a spherical aberration (SA), an astigmatism (AS), a distortion (DT), and a chromatic aberration of magnification (CC) respectively, of the example 6.

An endoscope objective optical system according to an example 6 will be described below. FIG. 7A is a diagram showing a cross-sectional view of a lens arrangement of the endoscope objective optical system according to the present example.

The endoscope objective optical system consists of in order from an object side, a front group GF having a positive refractive power, an aperture stop S, and a rear group GR having a positive refractive power.

The front group GF includes in order from the object side, a first lens L1 which is a planoconcave negative lens having a flat surface directed toward the object side, a second lens L2 which is a planoconvex positive lens having a flat surface directed toward an image side, an infrared absorbing filter F1, and a third lens L3 which is a planoconvex positive lens having a flat surface directed toward the object side. The aperture stop S is disposed between the front group GF and the rear group GR. The rear group GR includes a fourth lens L4 which is a biconvex positive lens, a fifth lens L5 which is a planoconcave negative lens having a flat surface directed toward the image side, and a sixth lens L6 which is a planoconvex positive lens having a flat surface directed toward the object side. A plane parallel plate F2 and a cover glass CG are disposed on the image side of the rear group GR. The sixth lens L6 is a field lens.

Moreover, a YAG laser cut coating is applied to an object side of an infrared absorbing filter F1, and a semiconductor laser cut coating is applied to an image side of the infrared absorbing filter F1.

Here, the fourth lens L4 having a positive refractive power and a fifth lens L5 having a negative refractive power are cemented, and form a cemented lens CL. Moreover, the plane parallel plate F2 is cemented to the cover glass CG formed on an image pickup surface I.

FIG. 7B, FIG. 7C, FIG. 7D, and FIG. 7E are aberration diagrams showing a spherical aberration (SA), an astigmatism (AS), a distortion (DT), and a chromatic aberration of magnification (CC) respectively, of the example 6.

Numerical data for each example is shown below. Regarding symbols, r denotes a radius of curvature (unit: mm), d denotes a distance between two lenses (unit: mm), ne denotes a refractive index of each lens for an e-line, vd denotes Abbe's number of each lens for a d-line, Fno denotes an F-number, and a stop denotes an aperture stop. An image plane corresponds to an image pickup surface.

EXAMPLE 1

Unit mm

Surface data

| Surface no. | r | d | ne | vd |
|---|---|---|---|---|
| 1 | ∞ | 0.3186 | 1.88815 | 40.76 |
| 2 | 1.2075 | 1.1470 | | |
| 3 | ∞ | 1.2744 | 1.52300 | 65.13 |
| 4 | ∞ | 0.2549 | | |
| 5 | 12.8638 | 1.5293 | 1.88815 | 40.76 |
| 6 | −2.6142 | 0.0478 | | |
| 7(Stop) | ∞ | 0.0478 | | |
| 8 | ∞ | 1.1948 | | |
| 9 | 7.5590 | 1.4815 | 1.88815 | 40.76 |
| 10 | −1.5309 | 0.4779 | 1.97189 | 17.47 |
| 11 | −8.0528 | 0.5066 | | |
| 12 | 5.6075 | 1.1789 | 1.51825 | 64.14 |
| 13 | ∞ | 0.0159 | 1.51500 | 64.00 |
| 14 | ∞ | 0.7965 | 1.61350 | 50.49 |
| 15(Image plane) | ∞ | | | |

Various data

| Focal length | 1.00 mm |
|---|---|
| Fno | 5.562 |
| Half angle of view | 80.4° |
| Object distance | 12.7 mm |
| Image height | 1.039 mm |

EXAMPLE 2

Unit mm

Surface data

| Surface no. | r | d | ne | vd |
|---|---|---|---|---|
| 1 | ∞ | 0.3580 | 1.88815 | 40.76 |
| 2 | 0.8418 | 1.0696 | | |
| 3 | 4.3245 | 1.3426 | 1.88815 | 40.76 |
| 4 | −2.4723 | 0.0448 | | |
| 5(Stop) | ∞ | 0.0448 | | |
| 6 | ∞ | 0.5967 | 1.52300 | 65.13 |
| 7 | ∞ | 0.7107 | | |
| 8 | 5.0719 | 1.2680 | 1.88815 | 40.76 |

-continued

Unit mm

| | | | | |
|---|---|---|---|---|
| 9 | −1.3779 | 0.4475 | 1.97189 | 17.47 |
| 10 | −4.9503 | 0.6742 | | |
| 11 | 5.2211 | 0.8950 | 1.51825 | 64.14 |
| 12 | ∞ | 0.0149 | 1.51500 | 64.00 |
| 13 | ∞ | 0.7459 | 1.61350 | 50.49 |
| 14 (Image plane) | ∞ | | | |

Various data

| | |
|---|---|
| Focal length | 1.00 mm |
| Fno | 4.583 |
| Half angle of view | 68.3° |
| Object distance | 11.9 mm |
| Image height | 0.973 mm |

EXAMPLE 3

Unit mm

Surface data

| Surface no. | r | d | ne | vd |
|---|---|---|---|---|
| 1 | ∞ | 0.3765 | 1.88815 | 40.76 |
| 2 | 1.1332 | 0.8964 | | |
| 3 | ∞ | 1.2549 | 1.52300 | 65.13 |
| 4 | ∞ | 0.3137 | | |
| 5 | ∞ | 1.5686 | 1.88815 | 40.76 |
| 6 | −2.3611 | 0.0471 | | |
| 7(Stop) | ∞ | 0.0471 | | |
| 8 | ∞ | 1.2489 | | |
| 9 | 5.8209 | 1.4588 | 1.88815 | 40.76 |
| 10 | −1.9255 | 0.5490 | 1.97189 | 17.47 |
| 11 | ∞ | 0.7792 | | |
| 12 | 2.5596 | 1.1765 | 1.51825 | 64.14 |
| 13 | ∞ | 0.0157 | 1.51500 | 64.00 |
| 14 | ∞ | 0.7843 | 1.61350 | 50.49 |
| 15(Image plane) | ∞ | | | |

Various data

| | |
|---|---|
| Focal length | 1.00 mm |
| Fno | 4.701 |
| Half angle of view | 80.4° |
| Object distance | 12.5 mm |
| Image height | 1.023 mm |

EXAMPLE 4

Unit mm

Surface data

| Surface no. | r | d | ne | vd |
|---|---|---|---|---|
| 1 | ∞ | 0.3819 | 1.88815 | 40.76 |
| 2 | 1.0411 | 0.9072 | | |
| 3 | ∞ | 0.9547 | 1.52300 | 65.13 |
| 4 | ∞ | 0.3182 | | |
| 5 | 7.1604 | 1.5912 | 1.88815 | 40.76 |
| 6 | −2.5519 | 0.0477 | | |
| 7(Stop) | ∞ | 0.0477 | | |
| 8 | ∞ | 0.8548 | | |
| 9 | 4.3737 | 1.4798 | 1.88815 | 40.76 |
| 10 | −1.5573 | 0.5569 | 1.97189 | 17.47 |
| 11 | ∞ | 0.5137 | | |
| 12 | 8.8633 | 0.7956 | 1.51825 | 64.14 |

-continued

Unit mm

| | | | | |
|---|---|---|---|---|
| 13 | ∞ | 0.0159 | 1.51500 | 64.00 |
| 14 | ∞ | 0.7956 | 1.61350 | 50.49 |
| 15(Image plane) | ∞ | | | |

Various data

| | |
|---|---|
| Focal length | 1.00 mm |
| Fno | 4.591 |
| Half angle of view | 80.4° |
| Object distance | 12.7 mm |
| Image height | 1.037 mm |

EXAMPLE 5

Unit mm

Surface data

| Surface no. | r | d | ne | vd |
|---|---|---|---|---|
| 1 | ∞ | 0.3816 | 1.88815 | 40.76 |
| 2 | 1.2607 | 1.3172 | | |
| 3 | −8.3502 | 0.8333 | 1.83932 | 37.16 |
| 4 | −3.7874 | 0.7949 | | |
| 5 | ∞ | 1.1423 | 1.88815 | 40.76 |
| 6 | −3.2268 | 0.0795 | | |
| 7(Stop) | ∞ | 0.0477 | | |
| 8 | ∞ | 0.6359 | 1.49557 | 75.00 |
| 9 | ∞ | 0.5873 | | |
| 10 | 5.4054 | 1.3514 | 1.88815 | 40.76 |
| 11 | −1.5808 | 0.4769 | 1.97189 | 17.47 |
| 12 | −8.5141 | 0.5984 | | |
| 13 | 5.5644 | 0.9539 | 1.51825 | 64.14 |
| 14 | ∞ | 0.0318 | | |
| 15 | ∞ | 0.7949 | 1.61350 | 50.49 |
| 16(Image plane) | ∞ | | | |

Various data

| | |
|---|---|
| Focal length | 1.00 mm |
| Fno | 3.060 |
| Half angle of view | 80.1° |
| Object distance | 19.1 mm |
| Image height | 1.037 mm |

EXAMPLE 6

Unit mm

Surface data

| Surface no. | r | d | ne | vd |
|---|---|---|---|---|
| 1 | ∞ | 0.3946 | 1.88815 | 40.76 |
| 2 | 1.0615 | 1.1566 | | |
| 3 | 4.7357 | 0.8344 | 1.85504 | 23.78 |
| 4 | ∞ | 0.0395 | | |
| 5 | ∞ | 0.4736 | 1.49557 | 75.00 |
| 6 | ∞ | 0.0395 | | |
| 7 | ∞ | 0.7893 | 1.88815 | 40.76 |
| 8 | −2.5233 | 0.0474 | | |
| 9(Stop) | ∞ | 0.0474 | | |
| 10 | ∞ | 0.5525 | | |
| 11 | 3.9748 | 1.0261 | 1.88815 | 40.76 |
| 12 | −1.7531 | 0.4736 | 1.97189 | 17.47 |
| 13 | ∞ | 0.0789 | | |
| 14 | ∞ | 0.7104 | 1.75844 | 52.32 |
| 15 | −6.0860 | 0.3092 | | |
| 16 | ∞ | 0.7893 | 1.51825 | 64.14 |

-continued

Unit mm

| | | | | |
|---|---|---|---|---|
| 17 | ∞ | 0.0158 | 1.51500 | 64.00 |
| 18 | ∞ | 0.5525 | 1.50700 | 63.26 |
| 19(Image plane) | ∞ | | | |

Various data

| | |
|---|---|
| Focal length | 1.00 mm |
| Fno | 3.662 |
| Half angle of view | 80.1° |
| Object distance | 18.9 mm |
| Image height | 1.029 mm |

Values of the conditional expressions of each of the embodiments are shown below.

| Conditional expression | Example 1 | Example 2 | Example 3 |
|---|---|---|---|
| (1) ff/f1 | −7.94 | −10.61 | −3.86 |
| (2) f1/f | −1.36 | −0.95 | −1.28 |
| (3) g1/g2 | 0.51 | 1.19 | 0.63 |
| (4) g1/f | 2.03 | 3.34 | 2.32 |
| (5) g2/f | 3.97 | 2.80 | 3.70 |
| (6) ff/f | 10.84 | 10.09 | 4.95 |

| Conditional expression | Example 4 | Example 5 | Example 6 |
|---|---|---|---|
| (1) ff/f1 | −14.55 | −7.56 | −6.71 |
| (2) f1/f | −1.18 | −1.42 | −1.20 |
| (3) g1/g2 | 0.39 | 0.69 | 0.65 |
| (4) g1/f | 1.94 | 2.45 | 2.35 |
| (5) g2/f | 4.96 | 3.54 | 3.64 |
| (6) ff/f | 17.12 | 10 | |

Various embodiments of the disclosure have been described heretofore. However, the disclosure is not restricted to the embodiments described heretofore, and embodiments in which the embodiments described heretofore are combined appropriately without departing from the scope of the disclosure are also in the scope of the disclosure.

The abovementioned endoscope objective optical system may satisfy a plurality of arrangements simultaneously. Doing so is desirable for achieving a favorable endoscope objective optical system. Moreover, the combinations of favorable arrangements are arbitrary. Furthermore, regarding conditional expressions, only an upper limit value or a lower limit value of a numerical range of more restricted conditional expression may be restricted.

As described heretofore, the disclosure is useful for an endoscope objective optical system and an endoscope having a wide angle and a small size, capable of dealing with an image sensor with a large number of pixels, while suppressing a degradation of performance due to the manufacturing error at the time of assembling an optical system.

According to the disclosure, it possible to provide an endoscope objective optical system and an endoscope having a wide angle and a small size, capable of dealing with an image sensor with a large number of pixels, while suppressing a degradation of performance due to the manufacturing error at the time of assembling an optical system.

What is claimed is:

1. An endoscope objective optical system comprising in order from an object side:
   a front group having a positive refractive power;
   an aperture stop; and
   a rear group having a positive refractive power, wherein
   the front group includes a negative lens which is nearest to an object,
   the rear group includes a positive lens which is nearest to an image,
   the negative lens has a planoconcave shape with a flat surface directed toward the object side, and
   the endoscope objective optical system satisfies following conditional expressions (1'''), (2), and (3''')

$$-15.0 < ff/f1 < -4.2 \tag{1'''}$$

$$-1.70 < f1/f < -0.95 \tag{2}$$

$$0.6 < g1/g2 < 1.20 \tag{3'''}$$

where,
ff denotes a focal length of the positive lens,
f1 denotes a focal length of the negative lens,
f denotes a focal length of the overall endoscope objective optical system,
g1 denotes a focal length of the front group, and
g2 denotes a focal length of the rear group.

2. The endoscope objective optical system according to claim 1, wherein the endoscope objective optical system satisfies following conditional expression (4)

$$1.2 < g1/f < 0.5 \tag{4}$$

3. The endoscope objective optical system according to claim 1, wherein the endoscope objective optical system satisfies following conditional expression (5)

$$2.5 < g2/f < 6.0 \tag{5}$$

4. The endoscope objective optical system according to claim 1, wherein the endoscope objective optical system satisfies following conditional expression (6)

$$4.0 < ff/f < 20.0 \tag{6}$$

5. The endoscope objective optical system according to claim 1, wherein the positive lens is one of, a lens cemented to a cover glass, and a lens disposed at a fixed distance from the cover glass.

6. An endoscope comprising:
   an endoscope objective optical system according to claim 1.

* * * * *